United States Patent
Takahashi (10) Patent No.: US 10,585,079 B2
(45) Date of Patent: Mar. 10, 2020

(54) CHLORINE-CONCENTRATION-MEASURING COMPOSITION

(71) Applicant: KURITA WATER INDUSTRIES LTD., Tokyo (JP)

(72) Inventor: Junichi Takahashi, Tokyo (JP)

(73) Assignee: KURITA WATER INDUSTRIES LTD., Tokyo (JP)

(*) Notice: Subject to any disclaimer, the term of this patent is extended or adjusted under 35 U.S.C. 154(b) by 338 days.

(21) Appl. No.: 15/038,813

(22) PCT Filed: Feb. 10, 2015

(86) PCT No.: PCT/JP2015/053631
§ 371 (c)(1),
(2) Date: May 24, 2016

(87) PCT Pub. No.: WO2015/146326
PCT Pub. Date: Oct. 1, 2015

(65) Prior Publication Data
US 2016/0377583 A1    Dec. 29, 2016

(30) Foreign Application Priority Data
Mar. 28, 2014 (JP) .................... 2014-070324

(51) Int. Cl.
*G01N 31/22* (2006.01)
*G01N 21/78* (2006.01)
(Continued)

(52) U.S. Cl.
CPC .......... *G01N 31/22* (2013.01); *G01N 33/182* (2013.01); *G01N 21/15* (2013.01); *G01N 21/78* (2013.01); *G01N 31/224* (2013.01)

(58) Field of Classification Search
CPC .... G01N 31/22; G01N 33/182; G01N 31/224; G01N 21/15; G01N 21/78
See application file for complete search history.

(56) References Cited

U.S. PATENT DOCUMENTS 3,912,457 A * 10/1975 Ogawa ................. G01N 33/728
                                               422/420
4,428,872 A    1/1984 Callicott
(Continued)

FOREIGN PATENT DOCUMENTS

CN    101120078 A    2/2008
CN    101864019 A    10/2010
(Continued)

OTHER PUBLICATIONS

PCT/ISA/210, "International Search Report for International Application No. PCT/JP2015/053631," dated Apr. 28, 2015.
(Continued)

*Primary Examiner* — Lyle Alexander
*Assistant Examiner* — Dwan A Gerido
(74) *Attorney, Agent, or Firm* — Manabu Kanesaka (57) ABSTRACT

An object of the present technology is to provide a chlorine-concentration-measuring composition that can reduce staining by reagents, a measurement method using the chlorine-concentration-measuring composition and a method for reducing staining by chlorine-concentration-measuring composition using an aromatic sulfonic acid-based polymer or the salt thereof.

Provided are a chlorine-concentration-measuring composition comprising an aromatic sulfonic acid-based polymer or the salt thereof; a chlorine-concentration-measuring composition comprising component (a) a color reagent for detection of residual chlorine and component (b) an aromatic sulfonic acid-based polymer or the salt thereof; a chlorine-concentration-measuring method comprising using the composition; and a method for reducing or preventing staining by using the chlorine-concentration-measuring composition comprising an aromatic sulfonic acid-based polymer or the salt thereof.

4 Claims, 2 Drawing Sheets

(51) Int. Cl.
*G01N 33/18* (2006.01)
*G01N 21/15* (2006.01)

(56) References Cited

U.S. PATENT DOCUMENTS

| | | | | |
|---|---|---|---|---|
| 4,562,148 A | * | 12/1985 | Sommer | G01N 33/525 |
| | | | | 422/400 |
| 5,637,508 A | * | 6/1997 | Kidwell | G01N 33/553 |
| | | | | 435/28 |
| 5,820,763 A | * | 10/1998 | Fujita | C23F 11/18 |
| | | | | 210/663 |
| 2007/0072305 A1 | * | 3/2007 | Mitsumoto | G01N 31/224 |
| | | | | 436/166 |
| 2010/0167412 A1 | * | 7/2010 | Xiao | B01L 3/0275 |
| | | | | 436/171 |
| 2012/0130195 A1 | * | 5/2012 | Martin | A61B 5/14507 |
| | | | | 600/300 |

FOREIGN PATENT DOCUMENTS

| | | |
|---|---|---|
| EP | 0 545 283 A1 | 6/1993 |
| EP | 2 757 417 A1 | 7/2014 |
| JP | S62-059752 B2 | 12/1987 |
| JP | H08-086782 A | 4/1996 |
| JP | H09-133671 A | 5/1997 |
| JP | 2002-350416 A | 12/2002 |
| JP | 2007-093399 A | 4/2007 |
| JP | 2007-286044 A | 11/2007 |
| JP | 2010-163661 A | 7/2010 |
| JP | 2012-011287 A | 1/2012 |
| JP | 2013-117038 A | 6/2013 |
| TW | 219352 B | 1/1994 |
| WO | 2013/039235 A1 | 3/2013 |

OTHER PUBLICATIONS

Taiwan Patent Office, "Office Action for Taiwanese Patent Application No. 104109649," dated Dec. 17, 2015.

* cited by examiner

CHLORINE-CONCENTRATION-MEASURING COMPOSITION

RELATED APPLICATIONS

The present application is National Phase of International Application No. PCT/JP2015/053631 filed Feb. 10, 2015, and claims priority from Japanese Application No. 2014-070324, filed Mar. 28, 2014, the disclosure of which is hereby incorporated by reference herein in its entirety.

TECHNICAL FIELD

The present technology relates to a chlorine-concentration-measuring composition, a chlorine-concentration-measuring composition kit, a chlorine-concentration-measuring method, and a method for reducing or preventing staining by chlorine-concentration-measuring reagent.

BACKGROUND ART

A chlorine agent such as sodium hypochlorite is added, for example, to daily life water such as tap water, stored water and pool water, and the like. Addition of such a chlorine agent is aimed at the effects such as sterilization and disinfection by its oxidative action. However, if there are suspended solids, organic matters, metal ions, or the like in the water, the chlorine agent reacts with these substances and diffuses into air in open systems such as water storage tanks and pools. It is thus needed for preservation of the effects to measure the residual chlorine concentration in the water to which the chlorine agent is added periodically and thus to assure that the chlorine agent is kept at a desired concentration.

In water treatment systems employing various filtration membranes such as microfiltration membrane, ultrafiltration membrane, and reverse osmosis membrane, the filtration membranes are easily degraded by oxidation if the chlorine agent is oxidized in the water to be treated. As oxidation of the filtration membrane leads to deterioration in water quality of the treated water, normally in such a water treatment system, an activated carbon filter apparatus or a sodium bisulfite-adding apparatus is installed upstream of the filtration membrane for removal of the chlorine agent from the water to be treated. It is needed then to monitor periodically the residual chlorine concentration in the water discharged from the activated carbon filter apparatus or the water to be treated containing added sodium bisulfite and examine whether the chlorine agent is decreased to a concentration without any problem or removed securely.

In the measurements for monitoring chlorine concentration in water described above, a color reagent that develops color in reaction with chlorine in water is used. Examples of the color reagents known include N,N-diethylphenylenediamine (DPD), benzidine compounds, and the like (see, for example, Patent Documents 1 to 3).

Claim 1 of Patent Document 1 describes "a chlorine-concentration-measuring composition, comprising the following components: (a) a particular benzidine compound represented by Formula (I) or the salt thereof and (b) a composition containing one or more substances selected from the group consisting of chelates and surfactants."

Claim 1 of Patent Document 2 describes "a composition for measuring the concentration of residual chlorine contained in water to be measured, comprising an aqueous solution containing a particular benzidine compound represented by Formula (I) and a surfactant, wherein the content of the surfactant is set to 0.5 mass % or more and 0.5 to 2.5 times by weight larger than that of the dialkylbenzidine compound and the pH is adjusted in an acidic range."

Claim 3 of Patent Document 3 describes "a method for determining residual chlorine amount, characterized by examining the residual chlorine amount in a test solution based on the color tone of the colorant generated when a solution containing a tetraalkylbenzidine or the salt thereof is mixed with the test solution."

The residual chlorine above is the sum of free chlorine (free residual chlorine) and bound chlorine (bound residual chlorine) and also referred to as total chlorine.

CITATION LIST

Patent Literatures

[Patent Document 1] JP-A No. 2002-350416
[Patent Document 2] JP-A No. 2007-286044
[Patent Document 3] JP-A No. H09-133671

SUMMARY OF INVENTION

Technical Problem

An object of the present technology is to provide a chlorine-concentration-measuring composition that can reduce staining by reagents, a measurement method using the chlorine-concentration-measuring composition, and a method for reducing staining by chlorine-concentration-measuring reagents using an aromatic sulfonic acid-based polymer or the salt thereof.

Solution to Problem

The present technology provides a chlorine-concentration-measuring composition comprising an aromatic sulfonic acid-based polymer or the salt thereof.

The present technology provides a chlorine-concentration-measuring composition comprising component (a) a color reagent for detection of chlorine, and component (b) an aromatic sulfonic acid-based polymer or the salt thereof.

The color reagent for detection of chlorine may be one or more compounds selected from the group consisting of phenylenediamine compounds, benzidine compounds, and the salts thereof.

The aromatic sulfonic acid-based polymer or the salt thereof may be one or more polymers selected from the group consisting of aromatic vinyl compound sulfonic acid polymers, polycondensates of an aromatic sulfonic acid and an aldehyde, and the salts thereof.

The present technology provides a chlorine-concentration-measuring composition kit, comprising a composition A containing a color reagent for detection of chlorine and a composition B containing an aromatic sulfonic acid-based polymer or the salt thereof.

The present technology provides a chlorine-concentration-measuring method using the chlorine-concentration-measuring composition or the chlorine-concentration-measuring composition kit.

The present technology provides a method for reducing or preventing staining by chlorine-concentration-measuring reagents characterized by using an aromatic sulfonic acid-based polymer or the salt thereof.

The present technology provides a method for reducing or preventing staining by chlorine-concentration-measuring reagents characterized by using the chlorine-concentration-measuring composition or the chlorine-concentration-measuring composition kit.

Advantageous Effects of Invention

The present technology provides a chlorine-concentration-measuring composition that can reduce staining by reagents, a measurement method using the same, and a method for reducing or preventing staining by chlorine-concentration-measuring reagents by using an aromatic sulfonic acid-based polymer or the salt thereof.

DESCRIPTION OF EMBODIMENTS

Hereinafter, favorable embodiments of the present invention will be described in detail. However, the present technology shall not restricted by the embodiments shown below. The present technology can be altered arbitrarily within the scope disclosed herein.

When a composition containing a conventional chlorine-concentration-measuring color reagent is used in an instrument or a kit for measurement of chlorine concentration in water, the staining component derived from the color reagent deposits on the internal surface of measurement cell, easily leading to decrease of measurement accuracy. It is also tedious to clean the cell unit. The shape of the cell is not particularly limited and the cell may be made of a plastic, glass, or quartz.

In an instrument that measures continuously the residual chlorine concentration in water, the measurement unit is gradually stained not by the staining components in water to be measured, but by the stains mainly derived from the color reagent and others. Thus in optical measurement using a color reagent or the like, periodical cleaning is needed for removal of stains.

Although stains in water to be measured can be removed for example by filtering or the like, it was difficult to prevent the staining derived from the chlorine-concentration-measuring reagents.

As shown in [Examples] below, when conventional chlorine-concentration-measuring composition (e.g., Patent Document 2, etc.) containing a chlorine-concentration-measuring color reagent and a surfactant are used, there are generated precipitates caused by the reagents during the color reaction and the precipitates adhere as staining component to the cell region for measurement. In particular in the case of a continuously measuring instrument, the staining components easily accumulate in the cell and may also adhere to the channels. The deposition of the staining component in the cell or the channels leads to lowered measurement accuracy or unfavorable measurement.

For prevention of the deterioration of measurement accuracy, unfavorable measurement, channel clogging and others, it is needed to shorten the cycle of cleaning the cell and channels for example by purging and to shorten the cycle of exchanging the parts such as cells and, in the case of a continuous measuring instrument, for example to clean parts after disassembly of the instrument, which easily leads to deterioration of measurement operational efficiency.

After intensive studies for a composition and a method for measurement of chlorine concentration that can reduce or prevent staining by the chlorine-concentration-measuring reagents, the inventors have found, as shown below in Examples, that it is possible to reduce or prevent deposition of staining component onto the surface of the analytical cell and also prevent generation of the staining component during measurement of chlorine concentration by using an aromatic sulfonic acid-based polymer. It is because the aromatic sulfonic acid-based polymer can suppress adhesion of the reagent-derived precipitates in the analytical cell and channels during the color reaction, and disperse the staining component into the aqueous system, as the polymer is adsorbed on the surface thereof.

As it became possible according to the present technology to prevent deposition of the reagent-derived staining component, which could only be removed for example by filtering, in an instrument continuously measuring chlorine concentration in water, the present technology is advantageous in chlorine concentration measurement in an instrument continuously measuring chlorine concentration in water.

The present technology relates to a reagent for analysis of chlorine concentration in water to be measured, specifically to a chlorine-concentration-measuring composition comprising an aromatic sulfonic acid-based polymer.

The present technology also relates to a chlorine-concentration-measuring composition, comprising component (a) a color reagent for detection of chlorine, and component (b) an aromatic sulfonic acid-based polymer.

The chlorine-concentration-measuring composition according to the present technology can be used in chlorine concentration measurement, typically in measurement of residual chlorine (total chlorine) concentration, free chlorine concentration, and bound chlorine concentration.

The color reagent for detection of chlorine (hereinafter, referred to also as "component (a)") used in the present technology may be any compound if it can develop color with chlorine in water. Examples of the color reagents include phenylenediamine compounds, benzidine compounds, the salts thereof, and the like. Examples of the benzidine compounds include tetraalkylbenzidine compounds and dialkylbenzidine compounds.

The component (a) is preferably one or more compounds selected from the group consisting of N,N-diethylphenylenediamine, dialkylbenzidine compounds, tetraalkylbenzidine compounds, and the salts thereof.

The component (a) may be one or more compounds selected from the compounds described above.

The compound of the component (a) may be present as a salt, and a substance in the salt shape may be used as the composition according to the present technology. Alternatively, a hydrate or solvated derivative of the compound or the salt thereof may be used. Alternatively, any stereoisomer, a mixture of stereoisomers, racemic mixture, or the like may also be used.

The phenylenediamine compound represented by the following Formula (I) has absorption peaks at around 500 to 520 nm and around 540 to 560 nm during chlorine concentration measurement in the acidic range.

The benzidine compound represented by the following Formula (II) has absorption peaks at wavelengths around 360 to 380 nm, around 450 to 470 nm, and around 640 to 660 nm during chlorine concentration measurement in the acidic range.

The component (a) according to the present technology is, for example, (N,N-diethylphenylenediamine) represented by the following Formula (I), a compound represented by the following Formula (II), or the salt thereof (see, for example, Patent Documents 1 to 3).

[C.1]

(I)

[C.2]

(II)

$R^1$ to $R^8$ in Formula (II) are respectively the following groups (i) or (ii).

(i) [$R^1$ and $R^2$ each are an alkyl group having 1 to 6 carbon atoms. $R^3$ and $R^4$ each are an alkyl group having 1 to 6 carbon atoms or both of them are hydrogen atoms. $R^5$ and $R^6$ each are a hydrocarbon group having 1 to 8 carbon atoms or both of them are hydrogen atoms. $R^7$ and $R^8$ are each a hydrogen atom, a sulfohydrocarbon group having 1 to 8 carbon atoms that may contain one or more hydroxyl groups, or a carboxy hydrocarbon group that may have one or more hydroxyl groups and both of them are not hydrogen atoms.]

(ii) [$R^1$ and $R^4$ are both hydrogen atoms. $R^2$ and $R^3$ are each an alkyl group having 1 to 6 carbon atoms. $R^5$, $R^6$, $R^7$, and $R^8$ are all hydrogen atoms.]

The alkyl group having 1 to 6 carbon atoms represented by $R^1$, $R^2$, $R^3$, or $R^4$ is preferably a linear or branched alkyl group. Typical examples thereof include methyl, ethyl, propyl, isopropyl, butyl, isobutyl, sec-butyl, tert-butyl, pentyl, 1-methylbutyl, 2-methylbutyl, 3-methylbutyl, 1-ethylpropyl, tert-pentyl, 1,2-diethylpropyl, hexyl, and the like.

Examples of the hydrocarbon groups having 1 to 8 carbon atoms represented by $R^5$ and $R^6$ include alkyl groups having 1 to 6 carbon atoms (identical with the alkyl groups $R^1$ and $R^2$ above), benzyl, phenyl, alkylphenyl groups (the alkyl group in the group is identical with the alkyl group $R^1$ and $R^2$ above), and the like.

The groups $R^5$ and $R^6$ are preferably both hydrogen atoms or both methyl or ethyl groups. $R^5$ and $R^6$ are more favorably both ethyl groups.

The sulfohydrocarbon group having 1 to 8 carbon atoms that may have one or more hydroxyl groups represented by $R^7$ and $R^8$ is a hydrocarbon group (identical with the hydrocarbon group $R^5$ and $R^6$ above) that is substituted by one or more sulfonic acid groups. The sulfohydrocarbon group may be present as an alkali-metal salt.

The substitution site of the sulfonic acid group is not particularly limited and normally, it is preferably substituted at the terminal of the alkyl group or at the benzyl or phenyl group. When the sulfohydrocarbon group has one or more hydroxyl groups, there is no restriction on the substitution site and the number of the hydroxyl groups. Examples of the favorable sulfohydrocarbon groups include 2-sulfoethyl, 3-sulfopropyl, 2-hydroxy-3-sulfopropyl, 2-hydroxy-2-sulfoethyl, 4-sulfobutyl, 2,4-disulfobenzyl, and the like.

The carboxy hydrocarbon group having 1 to 8 carbon atoms represented by $R^7$ and $R^8$ that may contain one or more hydroxyl groups is a hydrocarbon group (identical with $R^5$ and $R^6$) that is substituted with a carboxy group. The carboxy hydrocarbon group may be present as an alkali-metal salt.

The substitution site of the carboxy group is not particularly limited and it is normally, preferably substituted on the terminal of the alkyl group or a benzyl or phenyl group. When the carboxy hydrocarbon group has one or more hydroxyl groups, there is no particular restriction on the substitution sites and the number of the hydroxyl groups. Examples of the favorable carboxy hydrocarbon groups include 2-carboxyethyl, 3-carboxypropyl, 2-hydroxy-3-carboxyp rop yl, 2-hydroxy-2-carboxyethyl, 4-carboxybutyl, 2,4-dicarboxybenzyl, and the like.

Among the dialkylbenzidine compounds represented by Formula (II) above, those, wherein $R^5$, $R^6$, $R^7$, and $R^8$ are all hydrogen atoms, $R^1$ and $R^4$ are both hydrogen atoms, and $R^2$ and $R^3$ are both alkyl groups having 1 to 6 carbon atoms (favorably methyl or ethyl group), are preferable, and ortho-tolidine (3,3'-dimethylbenzidine) is more preferable.

When the benzidine compound is a dialkylbenzidine compound and $R^1$ and $R^2$ are both alkyl groups having 1 to 6 carbon atoms, $R^3$ and $R^4$ are preferably both hydrogen atoms. Further, $R^1$ and $R^2$ are more preferably both methyl or ethyl groups.

When the benzidine compound is a tetraalkylbenzidine compound, the alkyl group represented by $R^3$ and $R^4$ having 1 to 6 carbon atoms is, for example, an alkyl group identical with $R^1$ and $R^2$ described above. Further, $R^3$ and $R^4$ are more preferably both methyl or ethyl groups.

Among the benzidine compounds represented by Formula (II) above, favorable as the dialkylbenzidine compounds (wherein, $R^7$ and $R^8$ are not both hydrogen atoms) are, for example, N,N'-bis(2-sulfoethyl)-3,3'-dimethylbenzidine, N,N'-bis(3-sulfopropyl)-3,3'-dimethylbenzidine, N,N'-bis(2-hydroxy-2-sulfoethyl)-3,3'-dimethylbenzidine, N,N'-bis(2-hydroxy-3-sulfopropyl)-3,3'-dimethylbenzidine, N,N'-bis(4-sulfobutyl)-3, 3'-dimethylbenzidine, N,N'-bis(3-sulfopropyl)-N,N'-diethyl-3,3'-dimethylbenzidine, N,N'-bis(2,4-disulfobenzyl)-3,3'-dimethylbenzidine, the alkali-metal salts thereof, and the like. Among the compounds above, those in the shape of sodium salt are particularly favorable, as they are superior in water-solubility and resistant to crystallization at room temperature.

Among the benzidine compounds represented by Formula (II) above, favorable as the tetraalkylbenzidine compounds (wherein $R^7$ and $R^8$ are not both hydrogen atoms) are, for example, N-(2-sulfoethyl) -3, 3', 5, 5'-tetramethylbenzidine, N-(3-sulfopropyl)-3, 3', 5, 5'-tetramethylbenzidine, N-(4-sulfobutyl)-3,3', 5,5'-tetramethylbenzidine, N-(2-hydroxy-2-sulfoethyl) -3, 3', 5, 5'-tetramethylbenzidine, N-(2-hydroxy-3-sulfopropyl) -3, 3', 5, 5'-tetramethylbenzidine, N-(2, 4-disulfobenzyl)-3, 3', 5, 5'-tetramethylbenzidine, N,N'-bis (2-sulfoethyl)-3,3', 5,5'-tetramethylbenzidine, N,N'-bis(3-sulfopropyl)-3,3', 5,5'-tetramethylbenzidine, N,N'-bis(4-sulfobutyl)-3, 3', 5, 5'-tetramethylbenzidine, N,N'-bis(2-hydroxy-2-sulfoethyl)-3,3', 5,5'-tetramethylbenzidine, N,N'-bis(2-hydroxy-3-sulfopropyl)-3,3', 5,5'-tetramethylbenzidine, N,N'-bis(2, 4-disulfobenzyl) -3, 3', 5, 5'-tetramethylbenzidine, the alkali-metal salts thereof, and the like. Among the compounds above, those in the shape of sodium salt are particularly favorable, as they are superior in water-solubility and resistant to crystallization at room temperature.

The benzidine compounds are normally used individually, but may be used in combination. When two or more benzidine compounds are used in combination, two compounds may be selected from the dialkylbenzidine compounds or from the tetraalkylbenzidine compounds. Alternatively, a dialkylbenzidine compound and a tetraalkylbenzidine compound may be used in combination.

The aromatic sulfonic acid-based polymer used in the present technology (hereinafter, referred to also as "component (b)") is a polymer having at least a structural unit derived from an aromatic sulfonic acid monomer or the salt thereof. The polymer is preferably a water-soluble polymer carrying anionic ions. The polymer is a polymer obtained by polymerizing at least an aromatic sulfonic acid or the salt thereof. The salt is, for example, an alkali-metal salt (such as sodium salt).

Examples of the aromatic sulfonic acid-based monomers include aromatic vinyl compound sulfonic acids such as styrenesulfonic acid, a-methylstyrenesulfonic acid, vinyltoluenesulfonic acid, and vinylnaphthalenesulfonic acid; 2-naphthalenesulfonic acid, the salts thereof, and the like.

Examples of the aromatic sulfonic acid-based polymers include aromatic vinyl compound sulfonic acid polymers, polycondensates of an aromatic sulfonic acid and an aldehyde, and the like.

Examples of the aromatic vinyl compound sulfonic acid polymers include homopolymers of an aromatic vinyl compound sulfonic acid and copolymers of an aromatic vinyl compound sulfonic acid and other monomers. Examples of the other monomers include acrylonitrile, maleic anhydride, and the like.

Examples of the aromatic vinyl compound sulfonic acid polymers include styrenesulfonic acid polymers, a-methylstyrenesulfonic acid polymers, vinyltoluenesulfonic acid polymers, vinylnaphthalenesulfonic acid polymers, and the like.

Examples of the polycondensates of an aromatic sulfonic acid and an aldehyde include nap hthalenesulfonic acid formalin condensates, arylphenolsulfonic acid formaldehyde condensates, phenolsulfonic acid formaldehyde condensates, anthraquinonesulfonic acid formaldehyde condensates, naphthalenesulfonic acid formaldehyde condensates, and the like.

The component (b) is preferably a styrenesulfonic acid polymer, a naphthalenesulfonic acid formalin condensate, or the salt thereof and a styrenesulfonic acid polymer or the salt thereof is more preferable.

The ratio of anionic region to hydrophobic region in the polymer of the component (b) is not particularly limited.

The weight-average molecular weight of the component (b) polymer is preferably 1,000 to 2,000,000, more preferably 2,000 to 200,000. The weight-average molecular weight of the polymer may be determined on a high-temperature GPC (Gel Permeation Chromatography) instrument.

The component (b) polymer is favorably a low-molecular weight polymer.

The content of the color reagent for detection of chlorine in the composition according to the present technology is not particularly limited, but preferably 0.05 to 10 mass %, more preferably 0.1 to 5 mass %, still more preferably 0.2 to 4 mass %.

The content of the aromatic sulfonic acid-based polymer or the salt thereof in the composition according to the present technology is not particularly limited, but preferably 0.05 to 20 mass %, more preferably 0.1 to 10 mass %, still more preferably 0.3 to 7 mass %.

The mass ratio of the component (a) color reagent for detection of chlorine to the component (b) aromatic sulfonic acid-based polymer or the salt thereof used in the present technology [component (a): component (b)] is preferably 1:0.1 to 5, more preferably 1:0.1 to 3.

The composition according to the present technology is not particularly limited in shape and may be either liquid, solid, or semisolid. The composition is preferably liquid, as it is possible to reduce the labor of the user in adjusting the reagent when it is liquid.

The present technology also related to a chlorine-concentration-measuring composition kit comprising a composition containing the component (a) and a composition containing the component (b). The contents of the component (a) and the component (b) and the use rate thereof are the same as those in the composition according to the present technology described above.

The composition according to the present technology may contain any other components in addition to the components (a) and (b) in the ranges that do not impair the advantageous effects of the present technology. Examples of the any other components include potassium iodide, residual chlorine-immobilizing components, reducing agents, buffer agents, chelating agents, masking agents, sensitizers, degradation inhibitors, antifoaming agents, bacteriostatic agents, and the like.

Potassium iodide has been used in measurement of residual chlorine (total chlorine) concentration and bound chlorine concentration.

The residual chlorine-immobilizing component is a compound that generates bound chlorines such as chloramines, chloroimines, and chloroimides in reaction with residual chlorine. Examples of the residual chlorine-immobilizing components include primary amines, secondary amines, the salts thereof, ammonium salts, and the like.

The buffer agent is preferably contained in an amount that brings the composition according to the present technology into the acidic range, when added to the water to be measured. The buffer agent is added in an amount that brings the composition favorably to pH 3 to 8, more favorably to pH 4 to 7. Examples of the buffer agents include inorganic and organic acids. Typical examples of the inorganic acids include non-oxidative and non-reductive acids such as sulfuric acid, hydrochloric acid, and phosphoric acid. Typical examples of the usable organic acids include citric acid, acetic acid, succinic acid, oxalic acid, maleic acid, and the like. These acids may be used alone or in combination of two or more.

It is also possible, by preparing a separate composition containing the any other components, to prepare a kit in combination of the composition according to the present technology and the composition containing the any other components.

In the case of the composition kit according to the present technology, the any other components may be prepared as a separate composition or blended adequately too each composition. These compositions may be mixed to the water to be measured simultaneously or separately during measurement.

The composition or the composition kit according to the present technology can be prepared by a known method.

The composition or the composition kit according to the present technology can be used in measurement of chlorine concentration in water.

The kind of the water of which the residual chlorine concentration is measured is not particularly limited, and various waters such as daily life water, pool water, industrial water, industrial process water, and discharges from water treatment system can be used.

As shown in Examples below, the composition or the composition kit according to the present technology causes a reduced amount of deposition in the cell of light-detecting unit and thus reduces the amount of the stains deposited on the cell or channels in the light-detecting unit even after long-term operation. Therefore, the composition or the composition kit according to the present technology is used favorably in chlorine-concentration-measuring instruments (such as portable measuring instruments, simplified measurement kits, automated measuring instruments, etc.).

The composition or the composition kit according to the present technology can be used according to a known chlorine concentration (mg-Cl/L) measurement techniques (specifically, common official method (see "Standard Methods for Examination of Water" edited by Water Environment Dept., Environmental Health Bureau, Ministry of Health, Labour and Welfare, Japan Water Works Assoc., 1993)). Favored is a method of coloring the chlorine-concentration-measuring color reagent quantitatively.

The chlorine-concentration-measuring method according to the present technology uses at least the color reagent for detection of chlorine and the aromatic sulfonic acid-based polymer or the salt thereof described above. Alternatively the chlorine-concentration-measuring method according to the present technology uses the chlorine-concentration-measuring composition according to the present technology or the chlorine-concentration-measuring composition kit according to the present technology described above. Preferably, the measurement is performed under the measuring condition of the official method described above.

For an example, a chlorine-concentration-measuring composition at least containing an aromatic sulfonic acid-based polymer is mixed with water to be measured. The free residual chlorine concentration (Cl-mg/L) is determined from the change in color generated by the chlorine-concentration-measuring color reagent, using a colorimeter or a colorimetric panel. Potassium iodide (residual chlorine-immobilizing component) is added additionally to and mixed with the mixture and the free residual chlorine concentration (Cl-mg/L) is determined using a colorimeter or a colorimetric panel. The free chlorine concentration can be determined from the change in color generated by the color reagent within several minutes (e.g., within 1 minute), while the total chlorine concentration can be determined from the change in color generated by the color reagent after several minutes (e.g., after 3 minutes).

It is possible to produce a residual chlorine-concentration-measuring composition kit by using the composition according to the present technology and a composition containing a residual chlorine-immobilizing component in combination.

In the chlorine-concentration-measuring method according to the present technology, the addition amount of the chlorine-concentration-measuring composition according to the present technology to the water to be measured is not particularly limited, but, for example, preferably 0.01 to 10 mass %, more preferably 0.1 to 5 mass %, still more preferably 0.2 to 4 mass %.

The addition amount of the color reagent for detection of chlorine used in the present technology to the water to be measured may be that of known measurement methods. The addition amount of the color reagent for detection of chlorine to the water to be measured is preferably adjusted to 0.001 to 0.5 mass %, more preferably 0.005 to 0.1 mass %, still more preferably 0.01 to 0.05 mass % with respect to the water to be measured.

In the chlorine-concentration-measuring method according to the present technology, the addition amount of the aromatic sulfonic acid-based polymer or the salt thereof (as aromatic sulfonic acid-based polymer sodium salt) to the water to be measured is preferably adjusted to 0.001 to 0.5 mass %, more preferably 0.001 to 0.1 mass %, still more preferably 0.002 to 0.05 mass % with respect to the water to be measured.

In the chlorine-concentration-measuring method according to the present technology, the pH of the water to be measured is preferably adjusted to 3 to 8, more preferably 4 to 7.

The addition amount of the color reagent for detection of chlorine described above, the addition amount of the aromatic sulfonic acid-based polymer or the salt thereof, and the timing of addition for pH adjustment are not particularly limited. These substances may be added simultaneously or separately and the pH adjusted adequately during chlorine concentration measurement.

The present technology, which can reduce or prevent staining by reagents, is favorably applied to instruments having a detection cell, more favorably to continuously measuring instruments that are more susceptible to staining.

The present technology may have the following configurations:

[1] a chlorine-concentration-measuring composition comprising an aromatic sulfonic acid-based polymer or the salt thereof;

[2] the chlorine-concentration-measuring composition according to [1] above, comprising the following components (a) and (b):

component (a): a color reagent for detection of chlorine and component (b): an aromatic sulfonic acid-based polymer or the salt thereof;

[3] the chlorine-concentration-measuring composition according to [2] above, wherein the color reagent for detection of chlorine is one or more compounds selected from the group consisting of phenylenediamine compounds, benzidine compounds, and the salts thereof;

[4] the chlorine-concentration-measuring composition according to [2] or [3] above, wherein the color reagent for detection of chlorine is one or more compounds selected from the group consisting of N,N-diethylphenylenediamine, dialkylbenzidine compounds, tetraalkylbenzidine compounds, and the salts thereof;

[5] the chlorine-concentration-measuring composition according to any one of [1] to [4] above, wherein the aromatic sulfonic acid-based polymer or the salt thereof is one or more compounds selected from the group consisting of aromatic vinyl compound sulfonic acid polymers, polycondensate polymers from an aromatic sulfonic acid and an aldehyde, and the salts thereof;

[6] a chlorine-concentration-measuring composition kit comprising the following compositions A and B:

composition A; a composition containing a color reagent for detection of chlorine, and composition B: a composition containing an aromatic sulfonic acid-based polymer or the salt thereof;

the color reagent for detection of chlorine is preferably that described in [3] or [4] above, wherein the aromatic sulfonic acid-based polymer or the salt thereof is preferably that described in [5] above;

[7] a chlorine-concentration-measuring method, comprising using the chlorine-concentration-measuring composition according to any one of [1] to [5] above or the chlorine-concentration-measuring composition kit described in [6] above;

[8] the chlorine-concentration-measuring method according to [7] above, comprising adjusting the pH of the water to be measured to 4 to 8.

[9] a method for reducing or preventing staining by chlorine-concentration-measuring reagents, characterized by using an aromatic sulfonic acid-based polymer or the salt thereof, wherein the aromatic sulfonic acid-based polymer is preferably a low-molecular weight polymer; and

[10] a method for reducing or preventing staining by chlorine-concentration-measuring reagents, characterized by using the chlorine-concentration-measuring composition according to any one of [1] to [5] above or the chlorine-concentration-measuring composition kit according to [6] above.

EXAMPLES

Hereinafter, typical examples and the like will be described, but it should be understood that the present invention (the present technology) is not limited to these examples.

Experimental Example 1

Comparative Examples 1 to 3 and Examples 1 to 4

Potable water of Nogi, Tochigi, Japan was used as the water to be measured.

The water to be measured was supplied continuously to a 3L sample solution tank at a rate of 3 L/h, allowing overflowing and the test was performed, as fresh sample was supplied thereto continuously.

In addition, anionic and nonionic surfactants that are generally considered superior in the efficiency of preventing staining were also evaluated.

A two-liquid-type chlorine-concentration-measuring reagent was used in the Experimental Example 1. Chlorine-concentration-measuring compositions (reagents 1 to 7) comprising a composition containing a color reagent for detection of chlorine (N,N-diethylphenylenediamine was used in the present Example. It will be referred to hereinafter also as chlorine-detecting reagent) and having a blending composition shown in Table 1 were prepared as the first liquid reagents used in the chlorine-concentration-measuring reagent. In addition, a composition comprising potassium iodide (7.5 mass %), sodium hydroxide (0.5 mass %), (anhydrous) trisodium citrate (20 mass %), CyDTA (0.02 mass %), and water (balance) was prepared as the second liquid reagent of the chlorine-concentration-measuring reagent.

The chlorine concentration was determined successfully with any one of the reagents above (wavelength: 550 nm).

Figure 1:
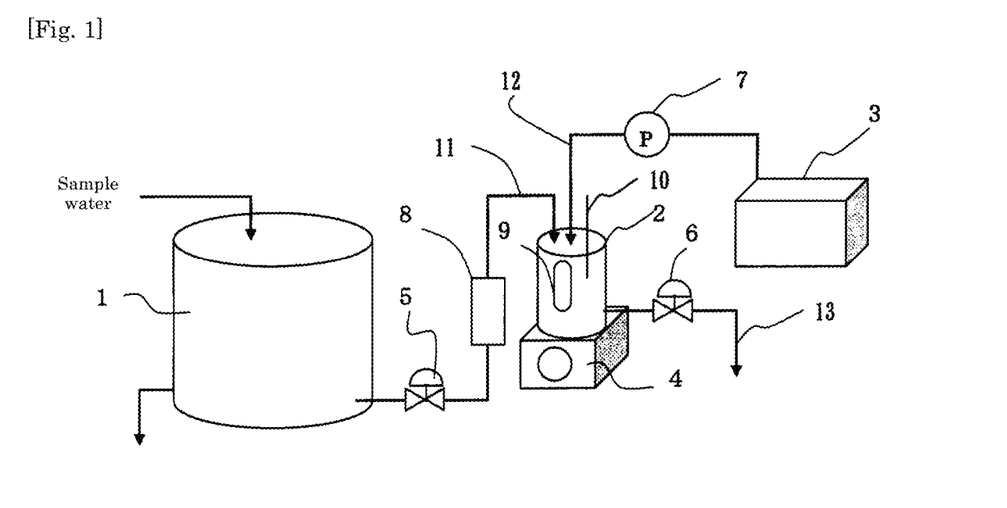
FIG. 1 is a view illustrating an instrument for measuring the residual chlorine concentration in water continuously.

FIG. 1 is a schematic view of a continuously measuring test instrument used for measurement of residual chlorine in the water to be measured using the chlorine-concentration-measuring compositions (reagents 1 to 7) shown in Table 1. The chlorine-concentration-measuring composition is placed in a measurement reagent tank 3 as the first liquid reagent of two-liquid-type chlorine-concentration-measuring reagent. Although not shown in the Figure, the second liquid reagent and a residual chlorine-immobilizing reagent are placed respectively in a second liquid reagent tank and a residual chlorine-immobilizing reagent tank and are fed to a measurement cell 2 through lines by pumps connected to the tanks during measurement of the residual chlorine concentration.

The test instrument has a line 11 installed for supplying the water to be measured (sample solution) in sample solution tank 1 to the measurement cell 2 via a constant-flow solenoid valve 5 and a flowmeter 8. It also has a line 12 installed for supplying the first liquid reagent in measurement reagent tank 3 to the measurement cell 2 via pump 7.

The measurement cell 2 has a transparent window 9 and a liquid surface sensor 10 installed.

In addition, the measurement cell 2 has on the bottom a stirring bar rotated by stirrer 4 (not shown in the Figure). The sample solution in the measurement cell 2 is discharged after chlorine concentration measurement through line 13 via solenoid valve 6. The wavelength used in measurement of the water to be measured after coloring reaction may be altered adequately according to the color reagent used.

<Chlorine Concentration Measurement>

Chlorine concentration measurement was performed in the test instrument according to the official method (see "Standard Methods for Examination of Water" edited by Water Environment Dept., Environmental Health Bureau, Ministry of Health, Labour and Welfare, Japan Water Works Assoc., 1993)).

(1) First, as the constant flow solenoid valve 5 was opened, the sample solution in the sample solution tank 1 was supplied via the flowmeter 8 and line 11 to measurement cell 2 having a capacity of 30 mL and when the liquid volume reached 20 mL, as the liquid volume was monitored by the liquid surface sensor 10, the constant flow solenoid valve 5 was closed.

(2) Subsequently, the first liquid reagent in the measurement reagent tank 3 and the second liquid reagent in the second liquid reagent tank were supplied by the pumps connected to the respective tanks in amounts respectively of 400 µL. with respect to the sample solution in the measurement cell 2 and the mixture was stirred and mixed, as the stirring bar was rotated by the stirrer 4. Additionally, a residual chlorine-concentration-immobilizing reagent was injected thereto and the mixture was stirred and mixed.

(3) After sufficient stirring and mixing, the color tone of the sample solution was measured through the transparent window 9 formed on the measurement cell 2, with a color tone analyzer prepared using a white LED and a RGB photosensor.

(4) The sample solution was then fed to and withdrawn from the measurement cell 2 repeatedly for ten times for sufficient cleaning of the interior of the cell 2.

(5) The operations (1) to (4) were repeated at an interval of five minutes.

The operations were performed continuously and the appearance of the measurement cell 2 was examined after 2, 4, and 6 weeks.

TABLE 1

|  |  | Reagent 1 | Reagent 2 | Reagent 3 | Reagent 4 | Reagent 5 | Reagent 6 | Reagent 7 |
|---|---|---|---|---|---|---|---|---|
| Blending composition (%) | DPD [1] | 3.0 | 3.0 | 3.0 | 3.0 | 3.0 | 3.0 | 3.0 |
|  | 97% Sulfuric acid | 3.0 | 3.0 | 3.0 | 3.0 | 3.0 | 3.0 | 3.0 |
|  | Polystyrenesulfonic acid polymer sodium salt [2] | 0 | 0 | 0 | 0.5 | 1 | 3 | 5 |
|  | SANNONIC FN100 [3] | 0 | 3 | 0 | 0 | 0 | 0 | 0 |
|  | SANDET ALH [4] | 0 | 0 | 3 | 0 | 0 | 0 | 0 |

[1] N,N-Diethylphenylenediamine
[2] A polymer having a molecular weight of 20,000, as determined on high-temperature GPC instrument, was used.
[3] SANNONIC FN100: polyoxyalkylene alkyl ether: nonionic surfactant
[4] SANDET ALH: sodium alkyldiphenylether disulfonate: anionic surfactant <Test Results>

Figure 2:
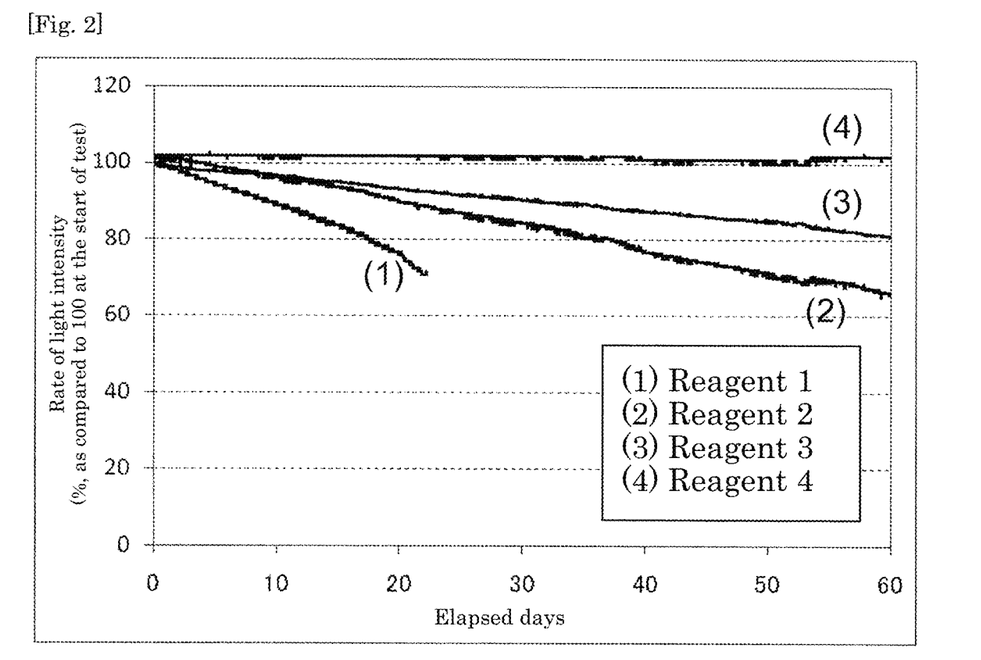
FIG. 2 shows the relationship between light intensity rate and elapsed days observed when the residual chlorine concentration in water was continuously measured using the instrument continuously measuring the residual chlorine concentration in water. The chlorine-concentration-measuring compositions in the Figure are (1) a conventional chlorine-concentration-measuring composition containing DPD, (2) a chlorine-concentration-measuring composition containing two kinds of reagents: DPD and a nonionic surfactant, (3) a chlorine-concentration-measuring composition containing two kinds of reagents: DPD and an anionic surfactant, and (4) a chlorine-concentration-measuring composition according to the present technology containing two kinds of reagents: DPD and an aromatic sulfonic acid-based polymer.

Test results are shown in Table 2 and FIG. 2. FIG. 2 shows the relationship between the rate of light intensity, as compared to 100% of the light intensity rate at the start of test, and the elapsed days, when the residual chlorine concentration of reagents 1 to 4 were determined using the test instrument.

When an anionic or nonionic surfactant, which was generally considered to be effective in preventing staining, was used, it was not possible to prevent generation or deposition of the reagent-derived staining component sufficiently for a long period of time, bringing the continuous measuring instrument into a state causing measurement error or unfavorable measurement (Comparative Examples 2 and 3).

In contrast, when an aromatic sulfonic acid-based polymer was used, it was possible to prevent generation or deposition of the reagent-derived staining component sufficiently for a long period of time, protecting the continuous measuring instrument from the state causing measurement error or unfavorable measurement (Examples 1 to 4). The content of the aromatic sulfonic acid-based polymer was preferably 0.5 to 5 mass % in the chlorine-concentration-measuring reagent and considered to be favorable when it is at least 0.5 mass %. The use ratio of the chlorine-detecting reagent to the aromatic sulfonic acid-based polymer was favorable at 3:0.5 to 5.

It was also favorable when the chlorine-detecting reagent was added to the water to be measured in an amount of 0.015 mass % and the aromatic sulfonic acid-based polymer in an amount of 0.0025 to 0.025 mass %.

Experimental Example 2

<Test Condition>

10 mL of purified water was placed in a 15 mL color comparison tube made of glass, 0.2 mL of a buffer agent (maleic acid salt) was added thereto, and the reagents shown in Table 3 were added respectively in amounts of 0.2 mL to respective test tubes. The pH then was in the range of 4 to 7. The reagents used were those shown in Table 3. The chlorine concentration measurement could be determined with any one of the reagents (wavelength: 550 nm).

After thorough tumbling and stirring, the mixture was left still at room temperature and the stains deposited on the bottom of the color comparison tube after 2 weeks were compared visually.

The buffer agent was prepared by dissolving maleic anhydride (15 g) and lithium hydroxide hydrate (11 g) with purified water to make 100 mL.

<Test Results>

Figure 3:
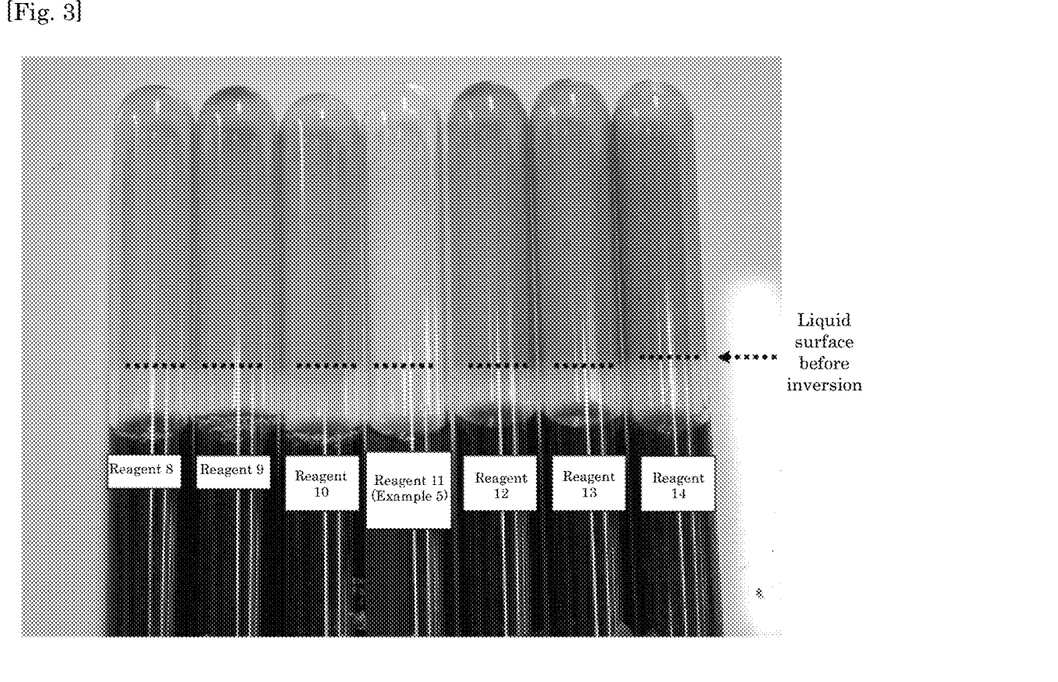
FIG. 3 shows the results of residual chlorine concentration measurements using respectively the chlorine-concentration-measuring compositions of reagents 8 to 14, wherein the test tubes containing the solutions after color development are placed upside down. Reagent 11 (Example 5) is a chlorine-concentration-measuring composition according to the present technology.

The amount of the staining component deposited on the glass surface increased in the order of: polystyrenesulfonic acid polymer (reagent 11) <SANDET ALH (reagent 8) <SANNONIC FN100 (reagent 10) <SANNONIC FN140 (reagent 9) <SEDORAN FF210 (reagent 12) <SEDORAN FF220 (reagent 13)≈blank (reagent 14) (see FIG. 3).

When the reagent containing the polystyrenesulfonic acid polymer (reagent 11/Example 5) was applied, there was almost no deposition on the wall, indicating that the reagent is most favorable.

It was also most favorable that, to the water to be measured, the chlorine-detecting reagent was added at a rate of 0.06 mass % and the aromatic sulfonic acid-based polymer was added at a rate of 0.04 mass %.

TABLE 2

|  | Comparative Example 1 Reagent 1 | Comparative Example 2 Reagent 2 | Comparative Example 3 Reagent 3 | Example 1 Reagent 4 | Example 2 Reagent 5 | Example 3 Reagent 6 | Example 4 Reagent 7 |
|---|---|---|---|---|---|---|---|
| At start of test | No deposition | No deposition | No deposition | No deposition | No deposition | No deposition | No deposition |
| After 10 days | Black deposit formed, causing measurement error | Trace amount of deposit formed | No deposition | No deposition | No deposition | No deposition | No deposition |
| After 4 weeks | Black deposit formed, causing measurement error | Trace amount of deposit formed, measurement continued | Extremely trace amount of deposit formed, measurement continued | No deposition | No deposition | No deposition | No deposition |
| After 6 weeks | Black deposit formed, causing measurement error | Black deposit formed, causing measurement error | Trace amount of deposit formed, measurement continued | No deposition | No deposition | No deposition | No deposition |
| After 8 weeks | Black deposit formed, causing measurement error | Black deposit formed, causing measurement error | Black deposit formed, causing measurement error | No deposition | No deposition | No deposition | No deposition |

TABLE 3

|  |  | Reagent 8 | Reagent 9 | Reagent 10 | Reagent 11 | Reagent 12 | Reagent 13 | Reagent 14 |
|---|---|---|---|---|---|---|---|---|
| Blending composition (%) | DPD [1] | 3.0 | 3.0 | 3.0 | 3.0 | 3.0 | 3.0 | 3.0 |
|  | Sulfuric acid (97%) | 1.0 | 1.0 | 1.0 | 1.0 | 1.0 | 1.0 | 1.0 |
|  | SANDET ALH [2] | 2.0 | 0 | 0 | 0 | 0 | 0 | 0 |
|  | SANNONIC FN140 [3] | 0 | 2.0 | 0 | 0 | 0 | 0 | 0 |
|  | SANNONIC FN100 [3] | 0 | 0 | 2.0 | 0 | 0 | 0 | 0 |
|  | Polystyrenesulfonic acid polymer [3] | 0 | 0 | 0 | 2.0 | 0 | 0 | 0 |
|  | SEDORAN FF210 [3] | 0 | 0 | 0 | 0 | 2.0 | 0 | 0 |
|  | SEDORAN FF220 [3] | 0 | 0 | 0 | 0 | 0 | 2.0 | 0 |
|  | BLANK | 0 | 0 | 0 | 0 | 0 | 0 | 2.0 |

[1] N,N-Diethylphenylenediamine
[2] SANDET ALH: sodium alkyldiphenylether disulfonate: anionic surfactant
[3] SANNONIC FN100, SANNONIC FN140, SEDORAN FF210, and SEDORAN FF220 have a composition of polyoxyalkylene ether: nonionic surfactants.
[4] A polymer having a molecular weight of 20,000, as determined on high-temperature GPC instrument, was used.

REFERENCE SIGNS LIST

1: Sample solution tank
2: Measurement cell
3: Measurement reagent tank
4: Stirrer
5: Constant flow solenoid valve
6: Sample solution-discharging solenoid valve
7: Pump
8: Flowmeter
9: Transparent window
10: Liquid surface sensor
11: Sample solution feed line
12: Measurement reagent feed line
13: Sample solution-discharging line

The invention claimed is:

1. A method for measuring chlorine concentration, comprising:
   mixing a chlorine-concentration-measuring composition comprising an aromatic sulfonic acid-based polymer or a salt thereof and a color reagent for detection of chlorine with water; and
   determining a free residual chlorine concentration from change in color generated by the color reagent.

2. A method for reducing or preventing staining by a chlorine-concentration-measuring reagent, comprising:
   mixing a chlorine-concentration-measuring composition comprising an aromatic sulfonic acid-based polymer or a salt thereof and a color reagent for detection of chlorine with water;
   suppressing adhesion of reagent-derived precipitates during color reaction; and
   dispersing a staining component into an aqueous system, as the polymer is adsorbed on a surface thereof.

3. A method for measuring chlorine concentration, comprising:
   mixing with water a composition A containing a color reagent for detection of chlorine and a composition B containing an aromatic sulfonic acid-based polymer or a salt thereof which a chlorine-concentration-measuring composition kit comprises; and
   determining a free residual chlorine concentration from change in color generated by the color reagent.

4. A method for reducing or preventing staining by a chlorine-concentration-measuring reagent, comprising:
   mixing with water a composition A containing a color reagent for detection of chlorine and a composition B containing an aromatic sulfonic acid-based polymer or a salt thereof which a chlorine-concentration-measuring composition kit comprises;
   suppressing adhesion of reagent-derived precipitates during color reaction; and
   dispersion a staining component into an aqueous system, as the polymer is adsorbed on the surface thereof.

* * * * *